US00PP25677P3

(12) United States Plant Patent
Higaki

(10) Patent No.: US PP25,677 P3
(45) Date of Patent: Jul. 7, 2015

(54) ***HYDRANGEA* PLANT NAMED 'BC7.12'**

(50) Latin Name: ***Hydrangea macrophylla* (Thunb.)**
Varietal Denomination: BC7.12

(71) Applicant: Harrison M. Higaki, San Mateo, CA (US)

(72) Inventor: Harrison M. Higaki, San Mateo, CA (US)

(73) Assignee: Bay City Flower Company, Inc., Half Moon Bay, CA (US)

( * ) Notice: Subject to any disclaimer, the term of this patent is extended or adjusted under 35 U.S.C. 154(b) by 69 days.

(21) Appl. No.: 13/986,047

(22) Filed: Mar. 25, 2013

(65) Prior Publication Data

US 2014/0289915 P1 Sep. 25, 2014

(51) Int. Cl.
*A01H 5/02* (2006.01)

(52) U.S. Cl.
USPC ..... Plt./250
CPC ..... *A01H 5/02* (2013.01)

(58) Field of Classification Search
USPC ..... Plt./250
CPC ..... A01H 5/02; A01H 5/00; A01H 1/02
See application file for complete search history.

*Primary Examiner* — June Hwu
(74) *Attorney, Agent, or Firm* — James R. Cypher; Charles R. Cypher

(57) ABSTRACT

A new and distinct cultivar of *Hydrangea macrophylla* (Thunb.) named 'BC7.12' originated as a controlled cross between varieties. The cultivar 'BC7.12' can be blue or red depending on the acidity of the soil and the presence of aluminum. The variety 'BC7.12' has compact, attractive inflorescences with relatively large sepalous florets, attractive sepal pigmentation which resists fading, long lasting blooms which set flowers evenly, stems that branch easily and are strong, and good commercial characteristics. When grown without aluminum, the upper sides of the sepals of the sepalous florets are primarily R.H.S. 67 A (red-purple group) and the under sides of the sepals are R.H.S 68 A (red-purple group).

3 Drawing Sheets

Botanical classification: *Hydrangea macrophylla* (Thunb.) 'BC7.12'.

Variety denomination: 'BC7.12'.

BACKGROUND OF THE INVENTION

This invention relates to a new and distinct cultivar of the Saxifragaceae family. The botanical name of the plant is *Hydrangea macrophylla* (Thunb.) 'BC7.12'.

The new cultivar originated as a seedling from a controlled cross between the unpatented variety 'LK49' and a commercial variety known as 'Venedig', the pollen parent, to the inventor which may be the subject of U.S. Plant Pat. No. 10,928 and registered as 'Venice Raven'. 'LK49', the seed parent, is relatively compact plant with wiry stems, relatively small leaves, relatively small sepalous florets, and inflorescences that are resistant to being damaged by conditions in commercial coolers.

The variety 'BC7.12' has compact, attractive inflorescences with relatively large sepalous florets, attractive sepal pigmentation which resists fading, long lasting blooms which set flowers evenly, and stems that branch easily and are strong. This combination of characteristics makes the plant ideal for commercial production as an ornamental potted plant. Below is a table comparing the new variety to similar varieties. The variety 'BC7.14' is the subject of a current patent application and has the same parents, although it was treated with aluminum. The new variety was grown alongside its parent 'Venedig' (grown as a pink variety) as a control. The new variety is generally taller than its parent 'Venedig'. 'Venedig' and the new variety have similarly sized inflorescences.

TABLE 1

| | New Variety 'BC7.12' | New Variety 'BC7.14' U.S. Plant Pat. No. 23,801 blued with aluminum | Commerical variety 'Venedig' which may be U.S. Plant Pat. 10,928 'Venice Raven' Grown without aluminum |
|---|---|---|---|
| Leaf size Plant height | 9 cm × 16.5 cm 17" in 6" pot. | 8 cm × 13.5 cm 14" in 6" pot. | Unknown 12" in 6" pot - observed controls grown alongside new variety. |
| Stem strength | Stems are strong. | Strong | Strong - observed controls grown alongside new variety |
| Sepal Pigmentation | Upper side of sepals is R.H.S. 67 A (red - purple group); Under side of sepals is R.H.S. 68 A (red-purple group). | Upper side of sepals is R.H.S. 94 A (violet - blue group) to 86 B (violet group); Under side of sepals is R.H.S. 93 D (violet group) to 86 C (violet group). | Upper side of sepals is R.H.S. 74 C (red - purple group). Under side of sepals is R.H.S. 75 B (purple group) observed controls grown alongside new variety. |
| Sepalous Floret Size | 60 mm | 50 mm | 50 mm - observed controls grown alongside new variety |

The new cultivar 'BC7.12' has been successfully asexually reproduced under controlled environmental conditions at a nursery in Half Moon Bay, Calif. under the direction of the inventor with its distinguishing characteristics remaining stable.

Asexual reproduction was first accomplished when vegetative stem cuttings were taken from the initially selected plant. Examination of asexually reproduced, successive generations grown in Half Moon Bay, Calif. show that the combination of characteristics as herein disclosed for 'BC7.12' remains firmly fixed.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
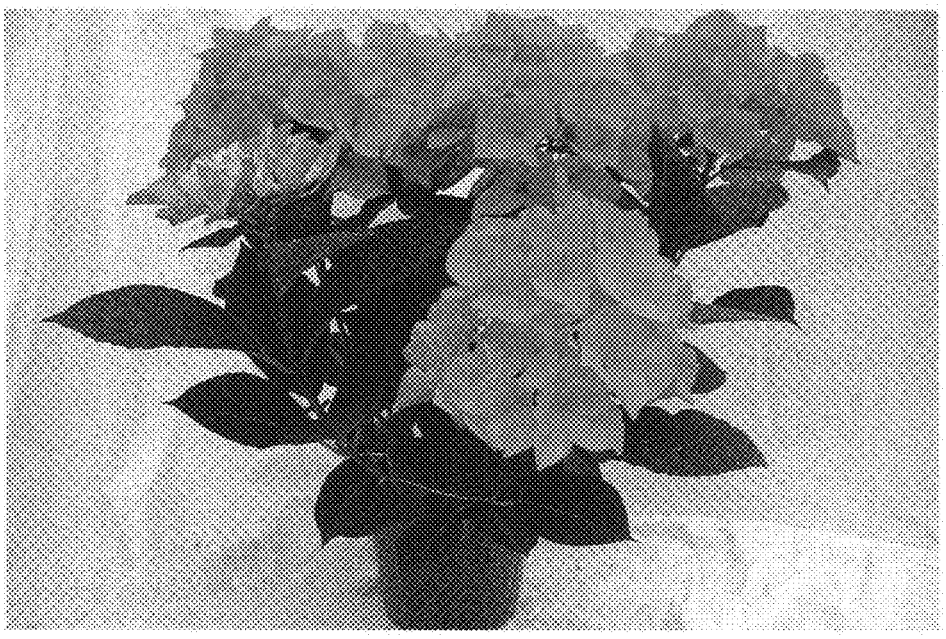
FIG. 1 is a view of the entire plant showing its form, growth habit, dark green foliage, inflorescence, and the color of its sepals.
Figure 2:
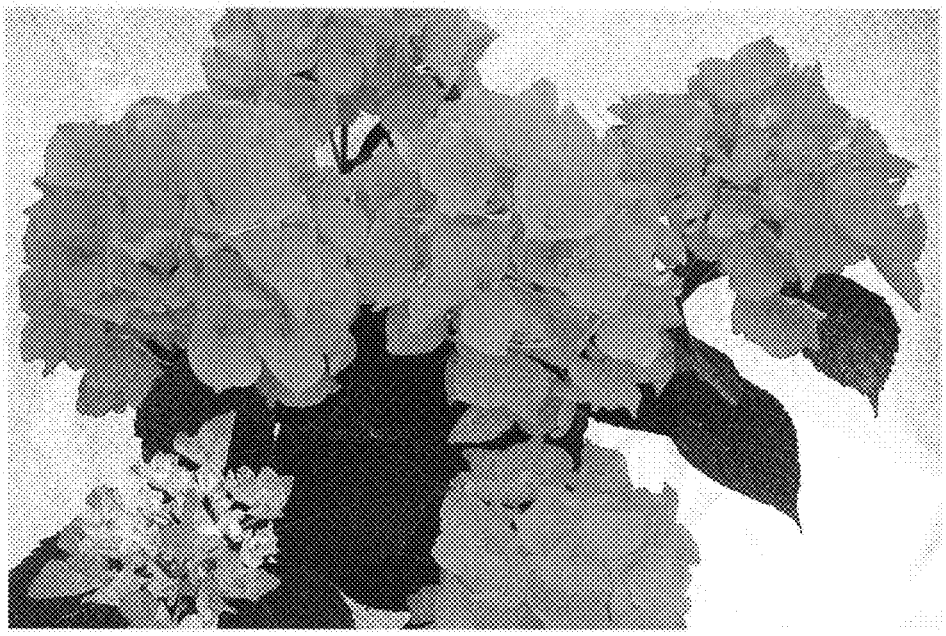
FIG. 2 is a view of the entire plant showing its form, growth habit, dark green foliage, inflorescence, and the color of its sepals.
Figure 3:
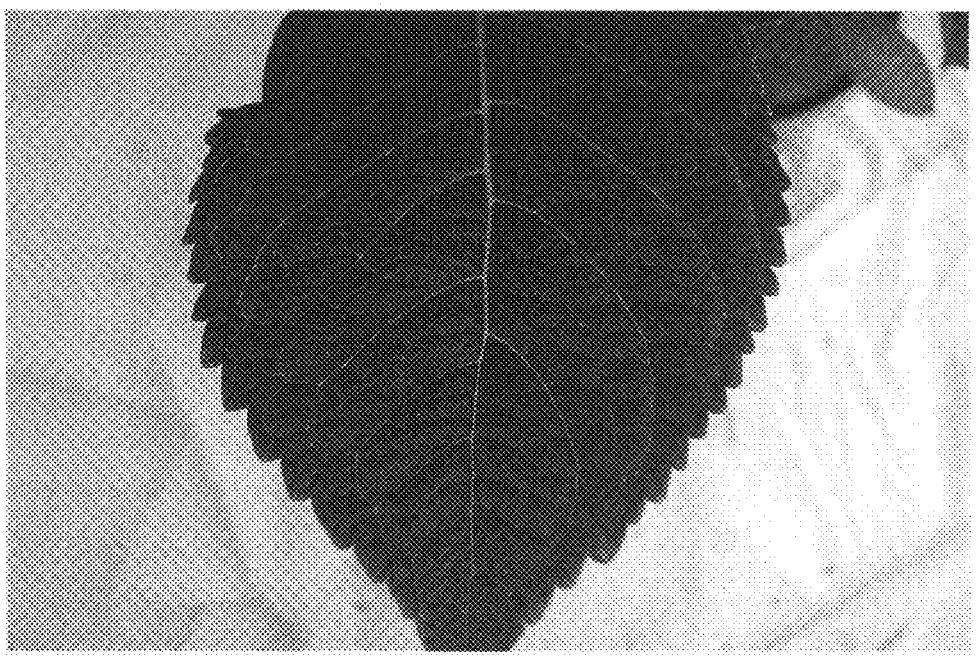
FIG. 3 is a close-up view of the adaxial surface of a mature leaf.
Figure 4:
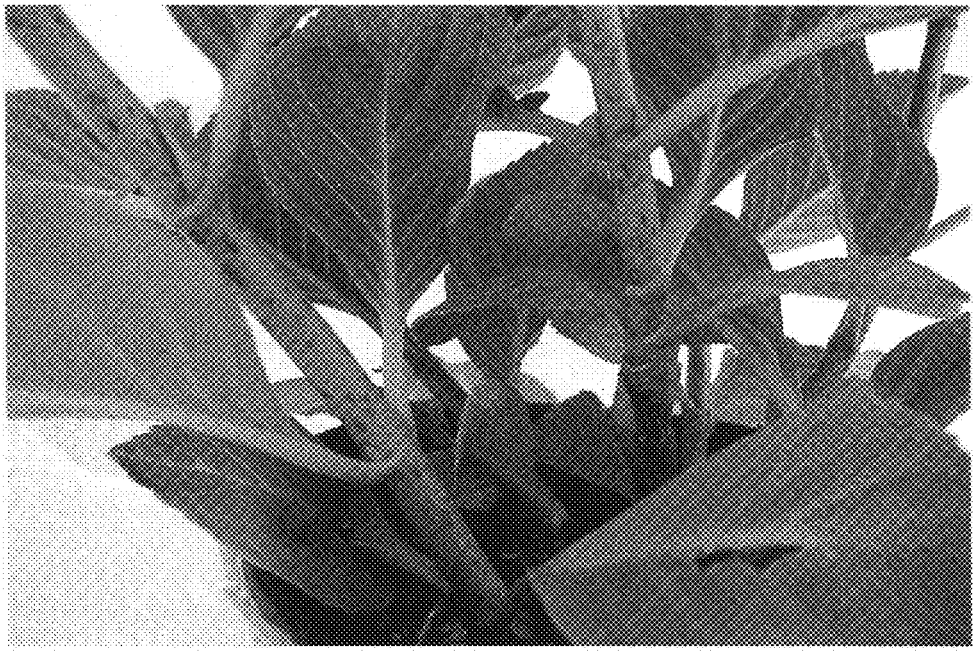
FIG. 4 is a close-up view of the base of the stem.
Figure 5:
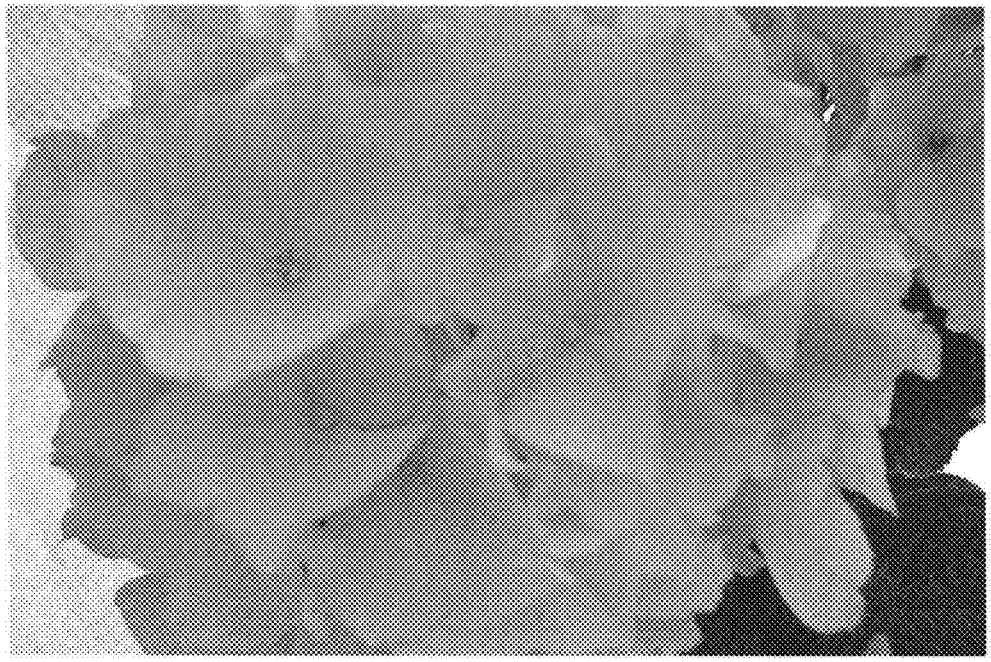
FIG. 5 is a close-up view of the upper side of a panicle of the new variety.
Figure 6:
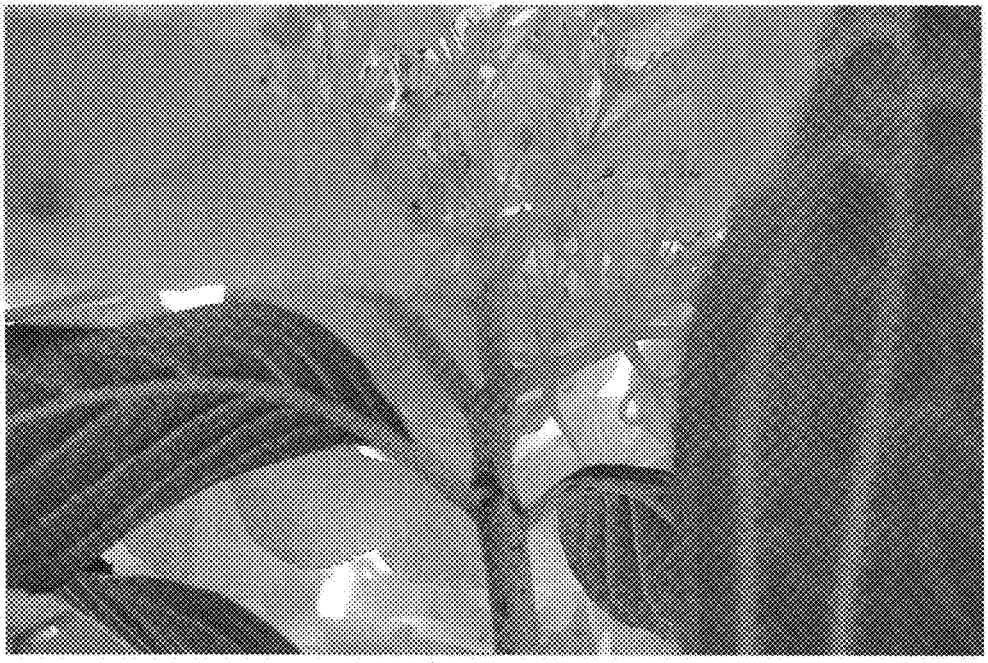
FIG. 6 is a close-up view of the center of a panicle of the new variety.

The plants shown in the figures are approximately one year old. The plant started out as cuttings, taken from the stem of a grown plant. The cuttings were placed in a pot and the soil was periodically fertilized. The plant was pinched early to promote lateral branches.

'BC7.12' has not been observed under all possible environmental conditions. The phenotype may vary significantly with variations in environment such as temperature, light intensity and day length. Color determinations were made with The Royal Horticultural Society (R.H.S.) Colour Chart, in association with the Flower Council of Holland, located in Lieden.

THE PLANT

Origin: Controlled cross. The new cultivar originated as a seedling from a controlled cross between the commercial variety known to the inventor as 'Venedig' and which may be 'Venice Raven', U.S. Plant Pat. No. 10,928, and the unpatented variety 'LK49'.

Form: Upright, compact shrub. A typical plant with a mature inflorescence that is ready for sale is approximately 17" high and has a diameter of 19" when grown in a 6" pot with appropriate soil amendments. Plants typically have 3 to 4 stems with one inflorescence between each stem.

Growth: Upright, vigorous growth habit. Inflorescence is large. The plant branches easily with shoots forming at the base of the plant. Lateral branches are similar in appearance and form to the main stems.

Stems: Lenticels are present. Lenticels are R.H.S. 86 A (violet group) and are 1 to 2 mm long. The surface of young stems is glabrous. Stems become woody as they age. The color of typical young stems and young lateral branches is R.H.S. 144 A (green group). The older portions of the stems are R.H.S. 199 A (grey-brown group) Younger portions of the stems are 5 to 7 mm in diameter. Older portions of the stems are 5 to 7 mm in diameter.

Foliage: Abundant. Leaves are opposite on stem and lateral branches.

*Shape of leaf.*—Elliptic with acute base and apex. Margins are serrate.

*Texture.*—Glabrous; veins dominate on the underside of the leaf and are sunken on the upper leaf surface.

*Color.*—Mature leaves have an upper side that is R.H.S. 147 A (yellow-green group), and an under side that is R.H.S. 138 B (green group). Leaves are pinnately veined. The midvein and veins branching off the midvein are large and prominent on the underside of the leaves. Veins are R.H.S. 144 D (yellow-green group). Leaves are as wide as 9 cm and 16.5 cm long. Petioles are smooth and 2.5 cm long and 4 mm wide. Petioles are R.H.S. 138 B (yellow-green group).

BUDS

Form: Globose with 3 to 5 connate, elliptic, smooth petals. Sepalous buds are more likely to have 4 petals. Non-sepalous florets are more likely to have 5 petals. Buds in the center of the inflorescence are non-sepalous. The majority of buds will develop into sepalous florets. Buds are approximately 1 mm by 1 mm when very young. Buds can be 4 mm in diameter and still unopened. Color of buds is R.H.S. 67 A (red-purple group).

Aspect: Unopened petals encasing buds are smooth.

Arrangement: Borne on branched panicles.

INFLORESCENCE

Form: Paniculate. Terminal. As many as 100 individual flowers (florets) per inflorescence. Both sepalous florets and non-sepalous florets borne on same panicle, with many more non-sepalous florets than sepalous florets. Flowers do not produce a fragrance. The peduncle for the inflorescence is strong and upright. Very few non-sepalous florets developing early on cymes that are later hidden by sepalous florets. Florets, both sepalous and non-sepalous, have anthers and style. Inflorescences are long-lasting, changing color as they age.

Size of inflorescence: Compact and globose. Individual inflorescence size is dependent on the number of florets. A typical inflorescence can grow as large as 8" in diameter, and 4" high.

Shape: Clusters of numerous small florets; sepalous florets overlap one another. Sepals are persistent.

Appearance: Showy.

FLORETS

General: The non-sepalous florets at the center of the inflorescence open first. Sepalous and non-sepalous florets are perfect and complete.

*Corolla.*—Generally, for both sepalous and non-sepalous florets the petals fall off as flower matures. Petals are typically 4 mm long and 3 mm wide. Petals are R.H.S. 75 A (purple group). Non-sepalous flowers are typically 4 mm in diameter after petals fall off. Lenticels that are very small are present on pedicels of both sepalous and non-sepalous florets. Lenticels are R.H.S. 59 B (red-purple) group. Pedicel of both sepalous and non-sepalous florets are primarily R.H.S. 67 A (red-purple group) when inflorescence is ready for commercial sale. Pedicels of non-sepalous florets are 4 mm long, and pedicels of sepalous florets are up to 40 mm long.

Stamens: 8 to 10 stamens, with more flowers having 10 stamens, for both sepalous florets and non-sepalous florets. Pollen is R.H.S. 158 C (yellow-white group). Plant produces abundant pollen. Filament is approximately 3 mm long. Filament is R.H.S. 78 A (purple group) and 6 to 7 mm long. Anther is 1 mm long and is regular and basally attached.

Stigma: Two to three style each, for both sepalous florets and non-sepalous florets. Each style has one stigma. Style is typically 1 mm long. For young inflorescences ready for commercial sale style is R.H.S. 68 A (red-purple group) and stigma is R.H.S. 78 A (purple group).

Ovary: Ovary is partially inferior, for both sepalous florets and non-sepalous florets.

Sepalous florets:

*General*. —Veins dominate on the underside of the sepals.

*Number of sepals*.—3 or 4 sepals per floret, usually 4.

*Aspect of Sepals*.—Smooth and glaucescent.

*Shape of sepals*.—Reniform with acuminate apex. Edges are entire, but with crenation.

*Size of sepals*.—As the florets mature, the sepals enlarge and overlap each other more and more, until, often, there is no space between the sepals when the petals of the florets open. Sepals at maturity are typically 40 mm long and 46 mm wide. Flowers are typically 6 cm in diameter. The upper sides of the sepals are primarily R.H.S. 67 A (red-purple group) and the under sides are primarily R.H.S. 68 A (red-purple group). Pink pigmentation develops at the tips of the sepals and travels inward towards the base of the sepals as the inflorescence matures.

Fruit: None.

Disease and pest resistance: Unknown.

I claim:

1. A new and distinct *Hydrangea macrophylla* plant named 'BC7.12' substantially as herein shown and described.

* * * * *